(12) United States Patent
Gunnsteinsson

(10) Patent No.: US 9,889,034 B2
(45) Date of Patent: Feb. 13, 2018

(54) ACHILLES TENDON STRETCHING DEVICE

(71) Applicant: OSSUR hf, Reykjavik (IS)

(72) Inventor: Larus Gunnsteinsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 54 days.

(21) Appl. No.: 14/457,553

(22) Filed: Aug. 12, 2014

(65) Prior Publication Data

US 2014/0350446 A1 Nov. 27, 2014

Related U.S. Application Data

(63) Continuation-in-part of application No. 13/173,496, filed on Jun. 30, 2011, now abandoned.

(60) Provisional application No. 61/453,633, filed on Mar. 17, 2011, provisional application No. 61/360,561, filed on Jul. 1, 2010.

(51) Int. Cl.
*A61F 5/01* (2006.01)
*A43B 7/14* (2006.01)
*A43B 7/16* (2006.01)
*A43B 17/02* (2006.01)

(52) U.S. Cl.
CPC .......... *A61F 5/0111* (2013.01); *A43B 7/144* (2013.01); *A43B 7/149* (2013.01); *A43B 7/1465* (2013.01); *A43B 7/16* (2013.01); *A43B 17/023* (2013.01); *A61F 5/0195* (2013.01)

(58) Field of Classification Search
CPC ....... A43B 7/144; A43B 7/1465; A43B 7/149; A43B 7/16; A43B 7/38; A43B 17/023; A61F 5/0111

USPC .............. 36/81, 92, 97, 110, 140, 142–144; 602/27
See application file for complete search history.

(56) References Cited

U.S. PATENT DOCUMENTS

| | | | |
|---|---|---|---|
| 1,674,687 A | 6/1928 | McCormick et al. |
| 2,184,209 A | 12/1939 | Burger |
| 2,212,414 A | 8/1940 | Burger |
| 2,509,423 A | 5/1950 | Cramer |
| 2,700,230 A | 1/1955 | Beyer |
| 3,124,887 A | 3/1964 | Vassar |
| 4,223,455 A | 9/1980 | Vermeulen |

(Continued)

FOREIGN PATENT DOCUMENTS

| | | |
|---|---|---|
| DE | 3520714 A1 | 12/1986 |
| DE | 9314920 A1 | 4/1994 |

(Continued)

OTHER PUBLICATIONS

International Search Report from corresponding International PCT Application No. PCT/US2015/041089, dated Oct. 5, 2015.

(Continued)

*Primary Examiner* — Sharon M Prange
(74) *Attorney, Agent, or Firm* — Workman Nydegger

(57) ABSTRACT

An Achilles heel wedge can include a single member having an anterior portion and a plurality of layers integrally connected at the anterior portion. A plurality of slits can differentiate the layers. Each slit can include a terminal end in the anterior portion having a perforation with a dimension greater than a width of the slit. The layers of the heel wedge can be selectively cut, ripped, or torn from the anterior portion of the heel wedge along the perforations to achieve incremental height adjustment of the heel wedge and stretching of the Achilles tendon.

14 Claims, 8 Drawing Sheets

(56) References Cited

U.S. PATENT DOCUMENTS

| | | |
|---|---|---|
| 4,942,677 A | 7/1990 | Flemming et al. |
| 4,955,370 A | 9/1990 | Pettine |
| 5,078,128 A | 1/1992 | Grim et al. |
| 5,133,776 A | 7/1992 | Crowder |
| 5,138,774 A | 8/1992 | Sarkozi |
| 5,152,081 A | 10/1992 | Hallenbeck et al. |
| 5,329,705 A | 7/1994 | Grim et al. |
| 5,399,152 A | 3/1995 | Habermeyer et al. |
| 5,437,111 A | 8/1995 | Kousaka et al. |
| 5,464,385 A | 11/1995 | Grim |
| 5,732,481 A | 3/1998 | Farhad |
| 5,782,015 A | 7/1998 | Dananber |
| 5,902,259 A | 5/1999 | Wilkerson |
| 5,954,075 A | 9/1999 | Gilmour |
| 6,503,178 B1 | 1/2003 | Gibbons |
| D483,556 S | 12/2003 | Zehr |
| 6,755,798 B2 | 6/2004 | McCarthy et al. |
| 6,984,197 B2 | 1/2006 | Sugiyama et al. |
| 7,198,610 B2 | 4/2007 | Ingimundarson et al. |
| 7,303,538 B2 | 12/2007 | Grim et al. |
| 8,061,548 B1 * | 11/2011 | Peggs .................... B65D 25/06 206/538 |
| 8,313,451 B2 | 11/2012 | Cox |
| 2001/0000369 A1 | 4/2001 | Snyder et al. |
| 2004/0019307 A1 | 1/2004 | Grim et al. |
| 2004/0259704 A1 | 12/2004 | Liang |
| 2005/0131324 A1 | 6/2005 | Bledsoe |
| 2005/0267603 A1 | 12/2005 | Lecomte et al. |
| 2007/0204487 A1 | 9/2007 | Clough |
| 2009/0287127 A1 | 11/2009 | Hu et al. |
| 2010/0042032 A1 | 2/2010 | Tomczak |
| 2010/0331749 A1 | 12/2010 | Powaser |
| 2011/0021963 A1 | 1/2011 | Graddon et al. |
| 2011/0087142 A1 | 4/2011 | Ravikumar et al. |
| 2012/0000092 A1 | 1/2012 | Ingvarsson et al. |
| 2012/0035520 A1 | 2/2012 | Ingimundarson et al. |
| 2013/0310721 A1 | 11/2013 | Hu et al. |

FOREIGN PATENT DOCUMENTS

| | | |
|---|---|---|
| DE | 10319480 A1 | 11/2004 |
| EP | 0409101 A2 | 1/1991 |
| GB | 2367763 A | 4/2002 |
| GB | 2429394 A | 2/2007 |
| JP | 7184968 A | 7/1995 |
| WO | WO 9204880 A1 | 4/1992 |
| WO | WO 2004009001 A1 | 1/2004 |

OTHER PUBLICATIONS

International Search Report from corresponding International PCT Application No. PCT/US2015/044434, dated Oct. 8, 2015.

"Bledsoe Achilles Boot Rise Kit, Application Instructions, Total Leg Support System with Infinite R.O.M. and Short Application Time," Council Directive 93/42/EEC of Jun. 14, 1993 concerning Medical Devices. http://www.bledsoebrace.com/products/achilles-boot/.

"This Boot is Made for Walking," the Rebound Air Walker by Ossur, Life Without Limitations, http://ww.ossur.com/lisalib/getfile.aspx?itemid+20244, 2010.

International Search Report and the Written Opinion of the International Searching Authority of International Application No. PCT/US2011/001168, dated Sep. 29, 2011.

\* cited by examiner

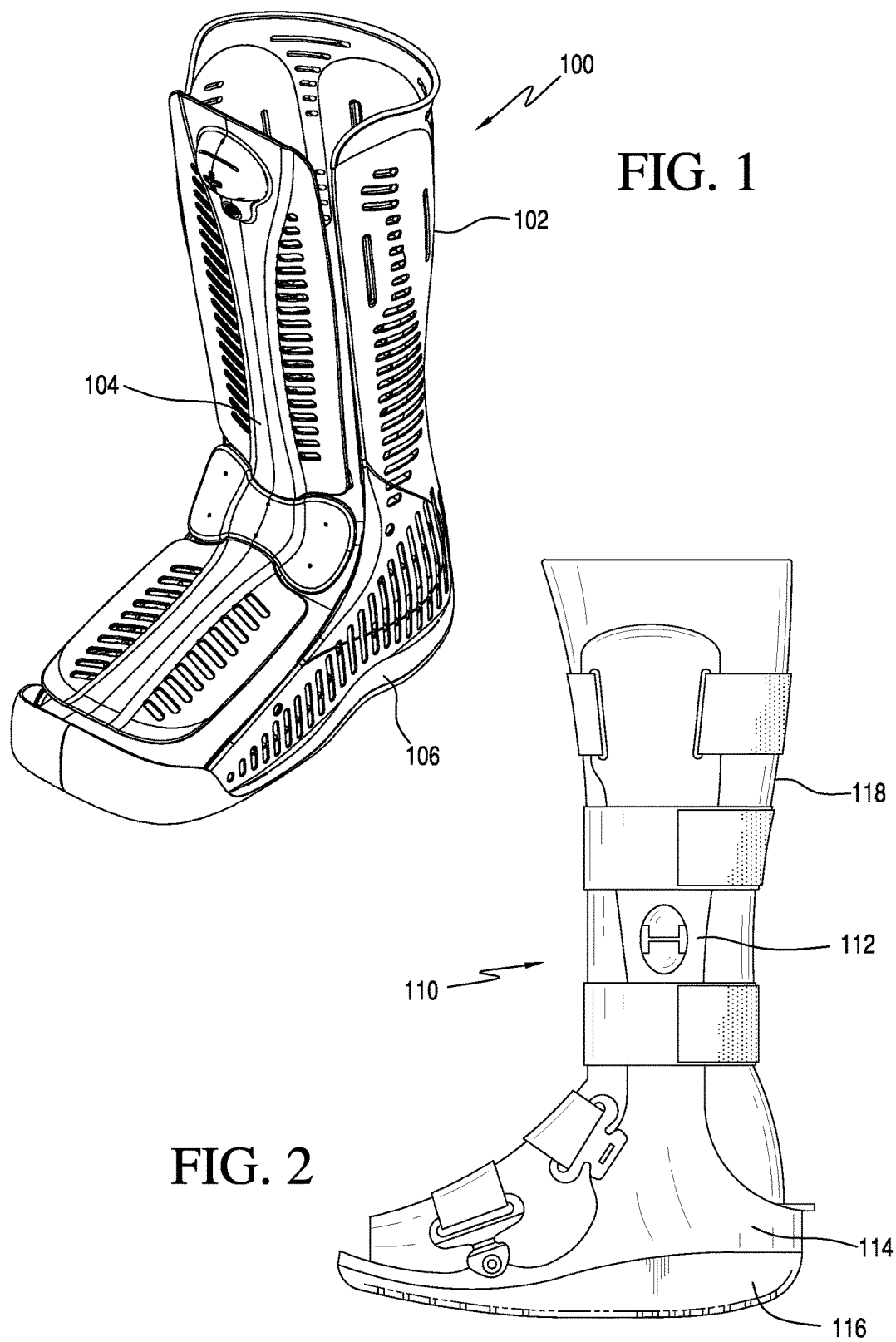

ACHILLES TENDON STRETCHING DEVICE

FIELD OF THE INVENTION

The present invention relates generally to the field of orthopedic or prosthetic devices and more particularly to a device for use in the treatment, repair, and rehabilitation of the Achilles tendon following an injury and/or corrective surgery.

BACKGROUND

Achilles tendon rupture is the most common injury involving a tear in a tendon. it commonly occurs as a sports injury during explosive acceleration, for example, while pushing off or jumping up.

Treatment of Achilles tendon rupture is typically divided between operative and non-operative management, each of which involve the gradual stretching of the tendon after the rupture has healed.

Operative management involves a surgical operation where the ruptured tendon is sutured back together at the point of rupture, and the leg is then placed into a cast. When the leg is placed in the cast, the foot is pointed downward (in an equinus position). As the healing progresses, the equinus position is then gradually decreased (requiring removal of the original cast, and recasting with the newly decreased equinus position).

Non-operative management typically involves wearing a cast or walking boot, which allows the ends of torn tendon to reattach themselves on their own. In the non-operative option, the foot is pointed downwards, with the help of heel wedges or insoles, which are placed in the walker boot. The height of the heel wedges or insoles is then incrementally decreased as the process of healing progresses. One disadvantage of using the heel wedges is that reducing the height of the wedges/insole can be too drastic for the injured tendon.

Both the operative and the non-operative methods involve a long rehabilitation process, lasting at least 6 months. Additionally, in each situation, removal of the cast or walking hoot is necessary in order to adjust the equinus position of the foot, and/or to remove and replace heel wedges or insoles having a different height.

Non-operative treatment might seem like a more comfortable way to go about Achilles repair, but it does take longer and leaves the patient with a greater risk of re-injury. Immobilization using a plaster cast can take as long as 12 months for the tendon to return to full strength, whereas surgery may only require anywhere from 6 to 9 months. In the past, patients who underwent surgery would wear a cast for approximately 4 to 8 weeks after surgery and were only allowed to gently move the ankle once out of the cast. Recent studies have shown that patients have quicker and more successful recoveries when they are allowed to move and lightly stretch their ankle immediately after surgery. To keep their ankle safe these patients use a removable boot while walking and doing daily activities.

In either the operative or the non-operative situation, existing methods for stretching the Achilles tendon can be time-consuming and inconvenient to implement. Additionally, existing methods for stretching the Achilles tendon can cause drastic changes in stretching the length of the Achilles tendon, such that the risk of re-rupture of the tendon is increased.

SUMMARY

In view of the above discussion, exemplary embodiments of an Achilles tendon stretching device are disclosed that provide improved mechanisms to allow more even stretching of the Achilles tendon, to reduce problems associated with edema, and to promote faster healing of the injured tendon in order to allow for faster recovery and shorter rehabilitation times.

Exemplary embodiments of an Achilles tendon stretching device can include manual or automatic mechanisms to allow incremental height changes to an insole placed within a walking boot, orthopedic shoe, or post-surgical shoe, in order to allow more even and gradual stretching of the Achilles tendon.

Exemplary mechanisms can include manual or automatic screw mechanisms, as well as manual or automatic pneumatic systems. Manual or automatic hydraulic systems are also contemplated.

Other exemplary mechanisms can include the use of a heel wedge having layers which can be torn or cut off to adjust the height of the heel wedge.

By utilizing the disclosed exemplary embodiments of an Achilles tendon stretching device, the degree of stretching of the tendon can be more easily and more evenly controlled, in order to avoid drastic changes in the stretched length of the tendon, which may lead to re-rupture of the tendon.

BRIEF DESCRIPTION OF THE DRAWINGS

These and other features, aspects, and advantages of the present invention will become better understood with regard to the following description, appended claims, and accompanying drawings where:

FIG. 1 is a perspective view of a circumferential type walking boot (walker) in which the exemplary embodiments of an Achilles tendon stretching device may be implemented;

FIG. 2 is a side view of another type of walker in which the exemplary embodiments of an Achilles tendon stretching device may be implemented;

Figure 3:
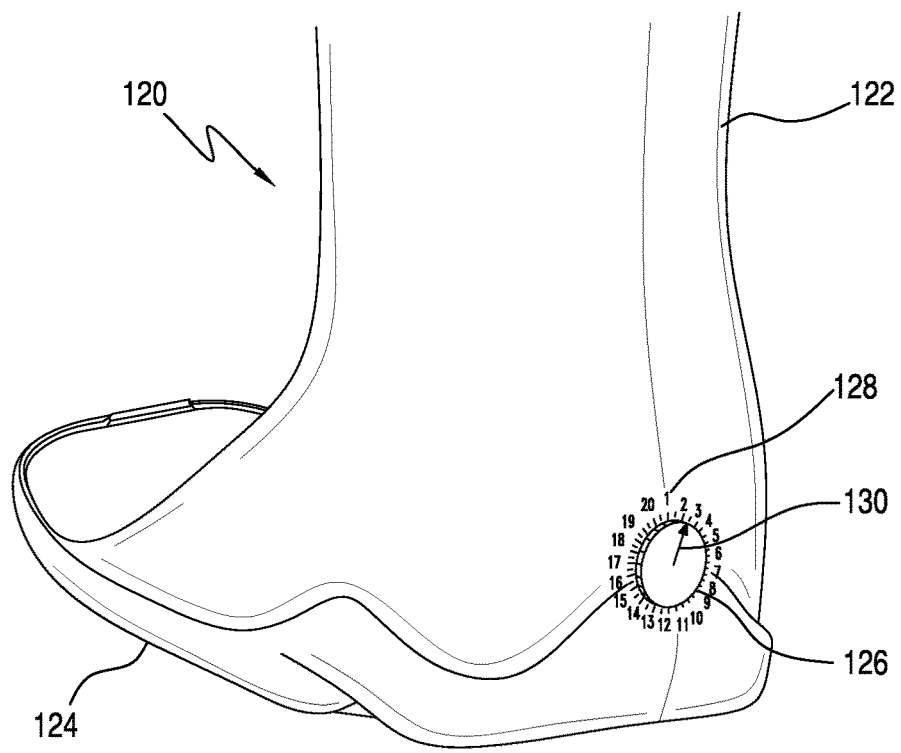
FIG. 3 is a rear perspective view of a first exemplary embodiment of an Achilles tendon stretching device implemented in a circumferential type walker.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of an Achilles tendon stretching device and the components thereof, and in no way limit the structures or configurations of an Achilles tendon stretching device and components thereof according to the present disclosure.

DETAILED DESCRIPTION

A. Environment and Context

Exemplary embodiments of an Achilles tendon stretching device are provided for use in the treatment, repair, and rehabilitation of the Achilles tendon following an injury and/or corrective surgery. Features that are provided on one side of the device can easily be provided on the other side of the device. In this manner, it is intended that the exemplary embodiments of the Achilles tendon stretching device described herein may be used on either right or left lower legs, with any appropriate reconfiguration of components that is deemed necessary for the proper fit and function of the device for the purpose of treatment, repair, and rehabilitation of the Achilles tendon of either the left or right lower leg.

In the exemplary embodiments of the Achilles tendon stretching device described herein, quick release strap mechanisms may be used to provide ease of securing and tightening the device to the lower leg. Exemplary quick release strap mechanisms are described in U.S. Pat. No. 7,198,610, granted April 2007, commonly owned, and herein incorporated in the entirety by reference.

The exemplary embodiments of the disclosure are adapted for treatment, repair, and rehabilitation of the Achilles tendon of human beings, and may be dimensioned to accommodate different types, shapes and sizes of human joints and appendages.

The exemplary embodiments of an Achilles tendon stretching device can be implemented in various configurations of walking boots, orthopedic shoes, or post-surgical shoes.

For example, exemplary embodiments of an Achilles tendon stretching device can be implemented within a circumferential type walker 100, as shown in FIG. 1. An exemplary circumferential type walker 100 includes a posterior shell 102 and an anterior, dorsal shell or plate 104, such that the lower leg is generally fully enclosed and supported by the walker 100. An outsole 106 is provided along the distal plantar surface of the walker 100.

Further, exemplary embodiments of an Achilles tendon stretching device can be implemented within a walker 110, as shown in FIG. 2. The walker 110 includes a sole portion 114 having supporting struts 112 extending therefrom, and an outsole 116. A liner 118 is provided enclosing the lower leg and positioned between and supported by the supporting struts 112.

Exemplary materials and configurations for components of the Achilles tendon stretching device, such as sole portions and shell portions, are described in detail in U.S. Pat. No. 5,078,128, granted January 1992, U.S. Pat. No. 5,329,705, granted July 1994, U.S Pat. No. 5,464,385, granted November 1995, and U.S. Pat. No. 7,303,538, granted December 2007, all commonly owned and incorporated herein in the entirety by reference. Additional exemplary materials and configurations for components of the Achilles tendon stretching device can be found in U.S. publication No. 2009/0287127, published Nov. 19, 2009, commonly owned, and herein incorporated in the entirety by reference.

For further ease of understanding the exemplary embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing, however, such support members or shells may have some degree of flexibility or resiliency.

B. First Exemplary Embodiment

Figure 4:
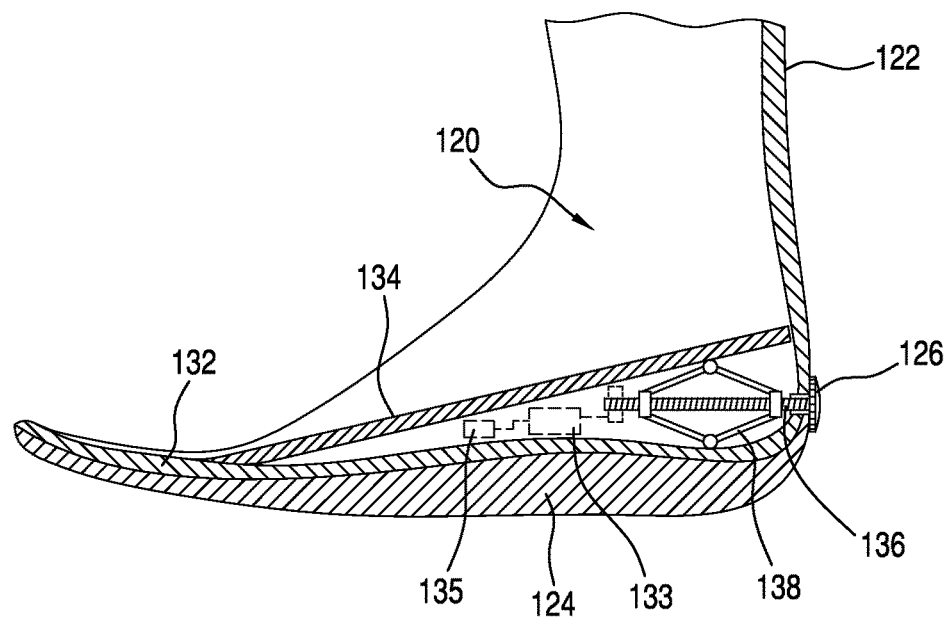
FIG. 4 represents a partial cut-away side view of the exemplary embodiment of an Achilles tendon stretching device shown in FIG. 3.

A first exemplary embodiment of an Achilles tendon stretching device is shown in FIGS. 3 and 4 as implemented in a generally circumferential walker 120 of the type shown in FIG. 1.

As shown, the walker 120 includes a posterior shell 122 and an outsole 124. An adjustment dial 126 is provided to allow adjustment of the height of an insole 134 in order to adjust the amount of stretching of the Achilles tendon.

In order to aid with determining the amount of stretching of the Achilles tendon, a marker 130 is provided on the adjustment dial 126 which points at distinct indicia 128, for example, numerical indicators, provided on the posterior shell 122 and/or the outsole 124. It will be recognized that the indicia may be provided on the adjustment dial 126 itself, and the marker may be provided on the posterior shell 122 or the outsole 124.

In order to provide a more even and less drastic stretching, each numerical indication of indicia 128 can represent a height change (increase or decrease) of 1 mm of the insole 134, such that each incremental movement of the adjustment dial 126 from one indicia to the next represents a change in height of the insole 134 of 1 mm. Of course, the height change represented by the incremental rotation of the adjustment dial 126 may be more or less than 1 mm.

As shown in FIG. 4, the adjustment dial 126 includes an adjustment screw 136 that can be connected to a scissor jack mechanism 138 positioned between the insole 134 and a plantar sole portion 132.

The adjustment dial 126 can be manually rotated, and may include appropriate textures or shapes to aid with manual manipulation, such as gipping thereof by the person adjusting the mechanism.

In the exemplary configuration, with manual adjustment of the adjustment dial 126, a practitioner or other authorized person can rotate the adjustment dial 126 one increment, once a week, in order to decrease the height of the insole 134 by 1 mm once every week in order to increase the amount of stretch of the Achilles tendon by 1 mm each week during use of the device. In this manner, a more even stretch of the Achilles tendon can be achieved, in order to avoid drastic changes in the stretched length of the tendon, which may lead to re-rupture of the tendon. With the exemplary configuration of the Achilles tendon stretching device, the walker 120 does not need to be removed from the patient in order to achieve adjustment thereof.

In a variation, an electric motor 133 (shown in outline in FIG. 4) may be provided, along with an appropriate control mechanism, in order allow for automatic adjustment of the adjustment dial 126. Such an adjustment may be made once a week, as discussed above, or may be accomplished in even smaller increments throughout a week in order to provide an even more gradual change in the amount of stretching of the Achilles tendon.

Appropriate onboard electronics (including, for example, sensors such as accelerometers, strain gauges, angle sensors, gyroscopes, etc.) and communication mechanisms (such as wireless Internet, Wi-Fi, Bluetooth, infrared, etc.) can be provided 135 (exemplarily shown in outline in FIG. 4) in order to sense the amount of activity of the user (and healing of the Achilles tendon), to automatically adjust the height of the insole 134 appropriately, and to provide communicative messages to a practitioner who may then remotely monitor the progress of the healing of the Achilles tendon.

In another variation of the Achilles tendon stretching device, instead of the adjustment dial 126, a socket head cap screw (or other suitable machine screw) can be provided as the adjustment screw 136.

C. Second Exemplary Embodiment

Figure 5:
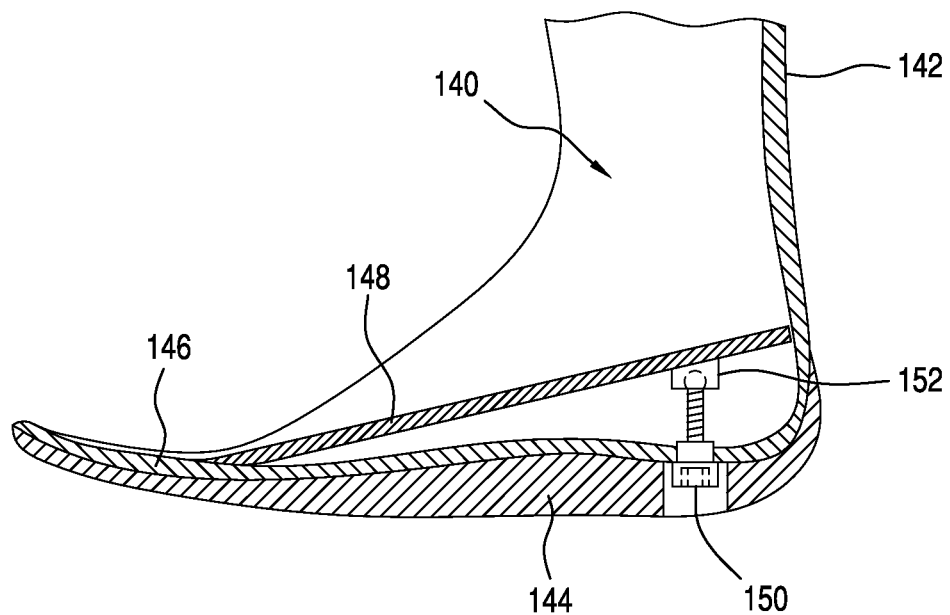
FIG. 5 represents a partial cut-away side view of another exemplary embodiment of an Achilles tendon stretching device.

In a second exemplary embodiment of an Achilles tendon stretching device shown in FIG. 5, a generally circumferential walker 140 has a posterior shell 142, a planter sole 146, and an insole 144.

In contrast to the embodiment shown in FIGS. 3 and 4, the adjustment mechanism is provided through the plantar sole 146 and the distal surface of the outsole 144. Additionally, instead of an adjustment dial, a socket head cap screw (or other suitable machine screw) is provided as the adjustment screw 150. The practitioner can utilize an Allen wrench in order to adjust the height of the insole 148 in order to adjust the amount of stretching of the Achilles tendon.

The far end of the adjustment screw 150 can be connected to the insole 148 by way of a universal joint 152, which allows rotation of the end of the adjustment screw 150, while providing a vertical translation of the insole 148.

Instead of the socket head cap screw, a dial with indicia, similarly to adjustment dial 126, may be used.

Rotation of the adjustment screw 150 to decrease the height of the insole 148 will cause the socket head portion of the adjustment screw 150 to become spaced from the plantar sole 146. The depth of the opening in the outsole 144 should be sufficient to accommodate the movement of the socket head portion of the adjustment screw 150.

Alternatively, an appropriate mechanical mechanism can be provided to cause the rotation of the adjustment screw 150 to be translated into the vertical height adjustment of the insole 148, without any corresponding vertical movement of the adjustment screw 150, such as, for example, a scissor jack mechanism.

Similarly as discussed above, an electric motor and associated control mechanisms can be provided in order to allow automatic (gradual and/or incremental) adjustment of the adjustment screw 150.

Figure 6:
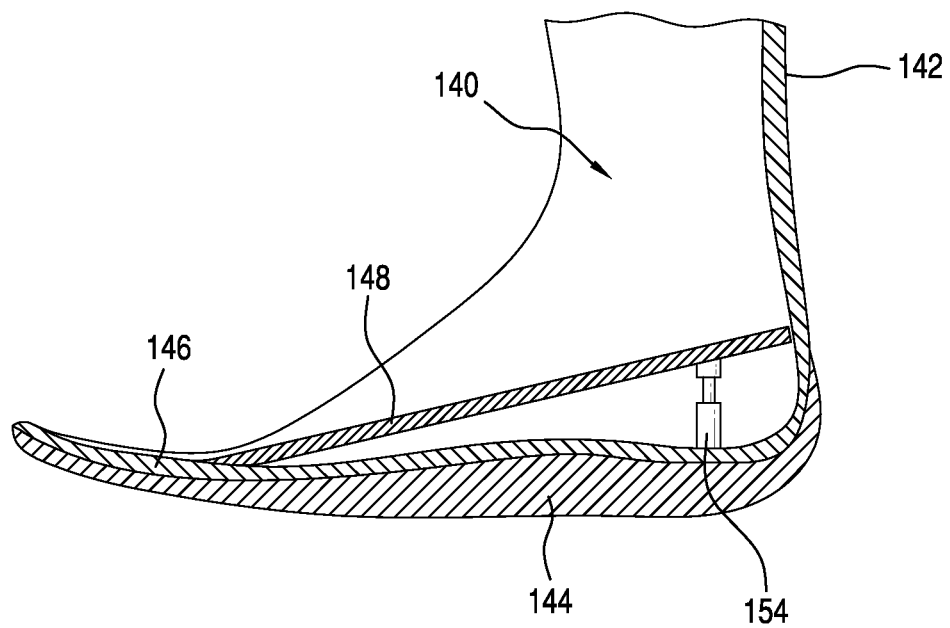
FIG. 6 represents a partial cut-away side view of another exemplary embodiment of an Achilles tendon stretching device.

In a variation shown in FIG. 6, the adjustment screw 150 may be replaced by a pneumatic or hydraulic piston and cylinder 154, which may be controlled in a known manner to achieve vertical height adjustment of the insole 148 with respect to the plantar sole 146.

Like the previously discussed embodiment, a practitioner can adjust this Achilles tendon stretching device once a week, in order to decrease the height of the insole 148 by 1 mm once every week in order to increase the amount of stretch of the Achilles tendon by 1 mm each week during use of the device. In this manner, a more even stretch of the Achilles tendon can be achieved, in order to avoid drastic changes in the stretched length of the tendon, which may lead to re-rupture of the tendon. Similarly, with this exemplary configuration of the Achilles tendon stretching device, the walker 140 does not need to be removed from the patient in order to achieve adjustment thereof.

D. Third Exemplary Embodiment

Figure 7:
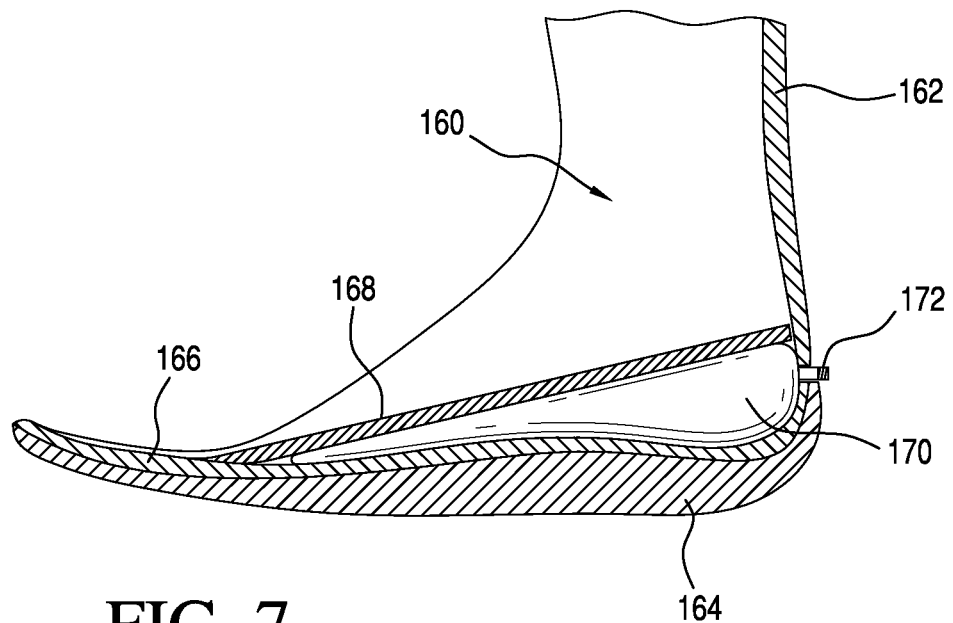
FIG. 7 represents a partial cut-away side view of another exemplary embodiment of an Achilles tendon stretching device.

A third exemplary embodiment of an Achilles tendon stretching device is shown in FIG. 7. In this embodiment, a walker 160 includes a posterior shell 162, a plantar sole 166, an outsole 164, and an adjustable height insole 168.

A pneumatic bladder 170 constructed of suitable materials capable of retaining a gas, such as air therein, is provided between the plantar sole 166 and the insole 168. A valve mechanism 172 is provided at the posterior of the bladder 170 and protruding through an opening in the posterior shell 162 for access thereto by a practitioner. Any suitable valve mechanism, such as, for example, a Schrader valve or a Presta valve, can be provided. It will be recognized that the valve mechanism 172 can alternatively be positioned to protrude through the plantar sole 166 and outsole 164.

Once a week, the patient can visit the practitioner, and the practitioner can release an appropriate amount of gas from the bladder 170, using the valve 172, in order to decrease the height of the insole 168 by an appropriate amount, for example, 1 mm.

Like the previously discussed embodiments, the walker 160 need not be removed from the patient in order to effectuate adjustment of the height of the insole 168. Similarly, a more even stretch of the Achilles tendon can be achieved, in order to avoid drastic changes in the stretched length of the tendon, which may lead to re-rupture of the tendon.

As a variation, a slow leak valve can be provided to automatically and continuously release a predefined amount of gas from the bladder 170 in order to automatically and gradually reduce the height of the insole 168, for example, an amount of 1 mm per week. Such a slow leak valve can be, for example, a slit valve designed to allow the slit to partially open in response to a continuous predefined pressure applied by the weight of the wearer of the walker 160. Alternatively, the slow leak valve can be any mechanical valve that can be set to an open or closed configuration, and which can be set in a slightly opened position to allow the slow leak. For example, any suitable ball valve, disc valve, butterfly valve, etc., may be utilized as a slow leak valve.

As a further variation, appropriate processor and automatic valve (for example, an electrically operated solenoid valve) mechanisms can be provided to effectuate gradual and/or incremental release of gas from the bladder 170.

Figure 8:
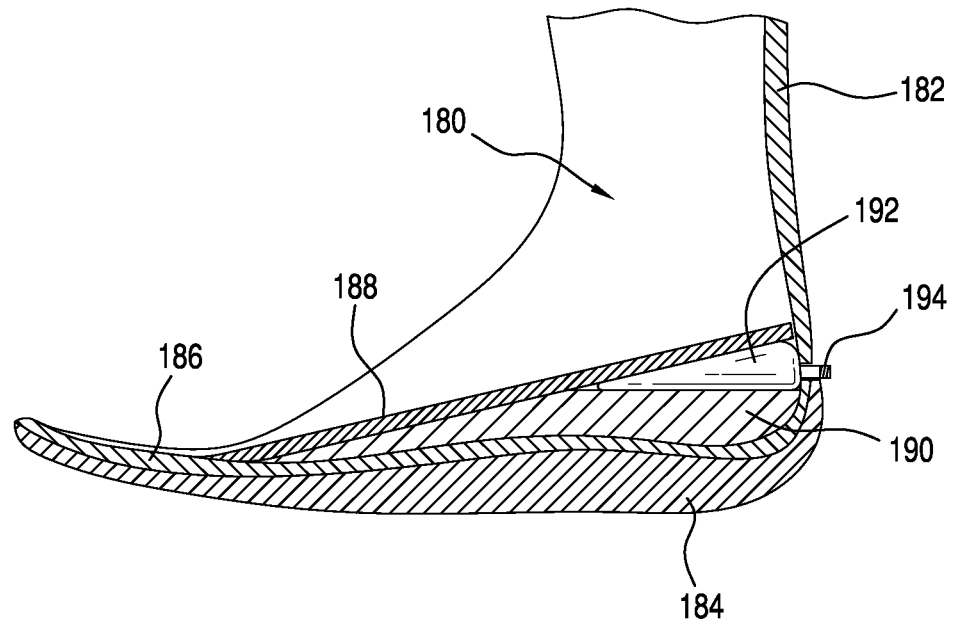
FIG. 8 represents a partial cut-away side view of another exemplary embodiment of an Achilles tendon stretching device.

In yet another variation, as shown in FIG. 8, a walker 180 includes a posterior shell 182, a plantar sole 186, an outsole 184, an adjustable height insole 188, and a bladder 192 having a valve 194. This variation of the Achilles tendon stretching device functions in generally the same manner as the device shown in FIG. 6, with the exception that in addition to the bladder 192 positioned between the plantar sole 186 and the insole 188, removable and interchangeable heel wedges 190 having different heights are provided (one at a time) between the bladder 192 and the insole 188 and the plantar sole 186. Alternatively, multiple heel wedges of consistent heights can be provided in place of the interchangeable heel wedges 190.

With this configuration and an automatically controlled release of gas from the bladder 192, the height of the insole 188 would gradually decrease throughout a week, and when the patient visits the practitioner, the heel wedge 190 can be replaced with a heel wedge of lower height (or one of the multiple heel wedges can be removed) and the bladder 192 can be reinflated.

While pneumatic bladders and valves are disclosed, it is contemplated that hydraulic bladders and valves may also be used.

Again, these configurations provide for a more even stretch of the Achilles tendon can be achieved, in order to avoid drastic changes in the stretched length of the tendon, which may lead to re-rupture of the tendon.

E. Fourth Exemplary Embodiment

Figure 9:
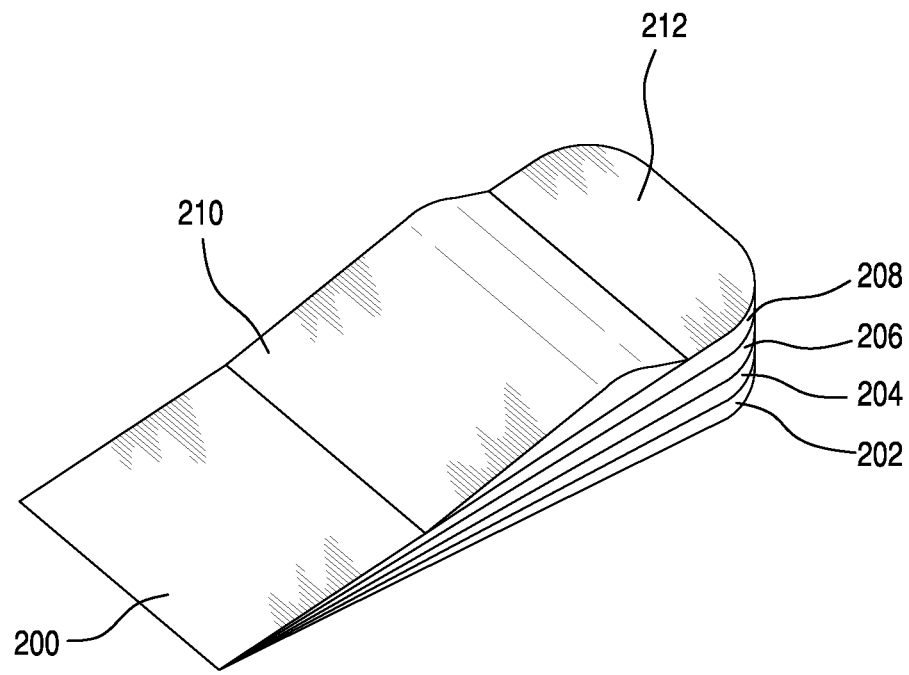
FIG. 9 represents a perspective view of another exemplary embodiment of an Achilles tendon stretching device in the form of a heel wedge having layers which can be torn or cut off to adjust the height of the heel wedge.
Figure 10:
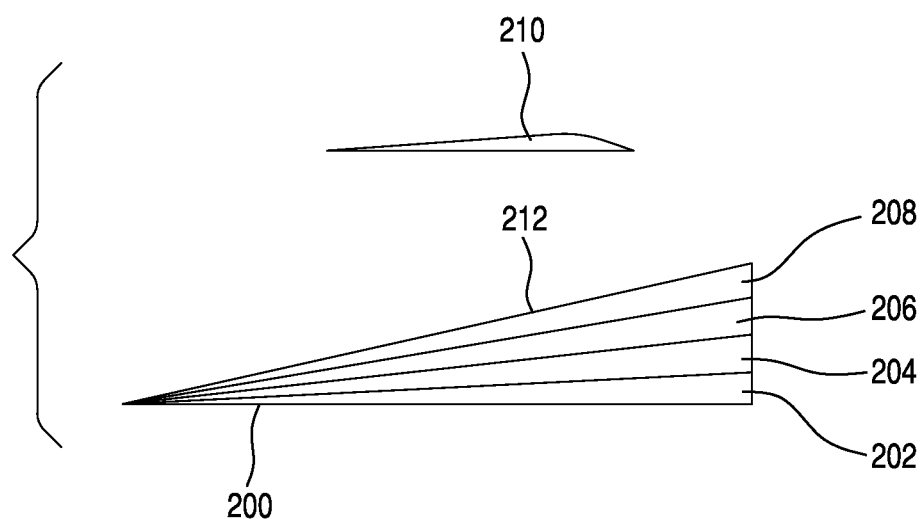
FIG. 10 is a partial exploded side view of the Achilles tendon stretching device shown in FIG. 9.

A fourth exemplary embodiment of an Achilles tendon stretching device in the form of a heel wedge 200 having layers 202, 204, 206, 208 which can be torn or cut off to adjust the height of the heel wedge is shown in FIGS. 9 and 10.

The heel wedge 200 can be used in any orthopedic device for use with the foot, for example, walkers, diabetic walkers, post-op shoes, ankle braces, or any type of footwear, such as shoes or boots.

The heel wedge 200 can be made from any suitable material, for example, ethylene-vinyl acetate (EVA) foam. Further, the heel wedge 200 can be made from compression molded EVA foam. Exemplary EVA foam can have a density/hardness in the range of 35-60 shore. Another suitable material may be an artificial cork, such as an EVA cork mixture that is thermo moldable at approximately 120 to 140 degrees and results in a density/hardness of 50 shore. Another exemplary material may be polyurethane.

As shown in FIGS. 9 and 10, the heel wedge 200 has a number of layers, all of which are integrally formed and connected together at an anterior portion of the heel wedge 200. As shown the heel wedge 200 includes first layer 202, second layer 204, third layer 206, and fourth layer 208. However, the number of layers shown is merely exemplary, and any suitable greater or lesser number of layers, for example, ten to fifteen layers, may be used in order to achieve the desired amount and increments of height adjustment.

In use, the heel wedge 200 can be positioned within the foot bed or heel portion of orthopedic device with all of the integrally formed layers thereof retained. Thus, the Achilles tendon of a user of the heel wedge 200 will be shortened to a first length.

In order to incrementally stretch the Achilles tendon of the user of the heel wedge 200, the layers 202, 204, 206, 208 thereof can be incrementally cut or torn from the heel wedge 200 in order to reduce the height of the heel wedge 200, thus stretching the Achilles tendon of the user to incrementally greater lengths.

The thickness or height of the layers 202, 204, 206, 208 corresponds to the desired incremental stretch length of the Achilles tendon, and may be any desired thickness or height.

In use, to adjust the stretch length of the Achilles tendon at a first time, the heel wedge 200 can be removed from the heel portion of orthopedic device. Then, the first layer 202 can be torn or cut away from the heel wedge 200, which can then be replaced in the heel portion of orthopedic device.

Treatment can then occur for the desired length of time to stretch the Achilles tendon at the length that is provided by removing the first layer 202 of the heel wedge 200. This process can be repeated as necessary by removing subsequent layers 204, 206, 208 in succession to treat Achilles tendon injuries and surgical recovery with incremental stretching of the Achilles tendon.

It is noted that if greater height adjustment is needed during a specified treatment period, more than one of the adjacent layers 202, 204, 206, 208 can be removed simultaneously. For example, after an initial treatment period using the heel wedge 200 having layers 202, 204, 206, 208, the adjacent first and second layers 202, 204 can be torn off of cut away in order to provide a greater height adjustment to increase the amount that the Achilles tendon is stretched.

This process can allow the use of a heel wedge 200 having numerous layers of minimal thickness, for example, 1 mm, for numerous treatment therapies for Achilles tendon injuries. Such a heel wedge and process can then be modified for each particular treatment protocol, where, for example, one protocol requires an incremental height adjustment of 1 mm per week, and another treatment protocol requires an incremental height adjustment of 5 mm per week.

For the treatment protocol requiring an incremental height adjustment of 1 mm per week, only a single layer of the heel wedge 200 would be removed each week. Similarly, for the treatment protocol requiring an incremental height adjustment of 5 mm per week, five of the layers of the heel wedge 200 would be removed each week.

Thus, in this manner, only one type of heel wedge 200 need be manufactured in order to satisfy numerous treatment protocols.

In order to provide additional stability to the Achilles tendon, and to prevent slipping of the user's heel within the orthopedic device and, therefore inadvertent stretching of the Achilles tendon, a heel stop 210 can be provided on the proximal surface 212 of the heel wedge 200.

The heel stop 210 can be formed, for example, from a compression molded EVA foam, or can be an injected molded thermoplastic elastomer (TPE), or any other suitable material.

As seen in FIGS. 9 and 10, the heel stop 210 can have a generally triangular shape, with a raised ridge provided on a proximal surface thereof, such that the raised ridge provides a stop against forward migration of the user's heel during use. In an alternative configuration, the heel stop 210 can have a generally trapezium or trapezoidal shape, such that a planar surface is provided at the raised ridge. The planar surface can thus provide an additional frictional surface to engage at least a portion of the arch of the user's foot in order to prevent slippage of the user's heel.

The heel stop 210 can be glued or secured with adhesive directly to the proximal surface 212 of the heel wedge 200. Alternatively, the heel stop 210 may be held in place on the proximal surface 212 of the heel wedge 200 by the weight of the user and frictional forces.

Thus, it can be seen that the heel wedge 200 having a number of layers, all of which are integrally formed and connected together at an anterior portion of the heel wedge 200, and which can be selectively removed as desired to achieve incremental height adjustment and stretching of the Achilles tendon provides a convenient and simple way to affect treatment and recovery for Achilles tendon injuries and surgeries.

F. Fifth Exemplary Embodiment

A fifth exemplary embodiment of an Achilles tendon stretching device comprises an Achilles heel wedge 300 including one or more perforations which provide stress relief to the heel wedge 300 and/or aid in removal of the layers. Like the heel wedge 200, the heel wedge 300 can be used in any orthopedic device for use with walkers, diabetic walkers, post-op shoes, ankle braces, or any type of footwear, such as shoes or boots. Similarly, the heel wedge 300 can be made from any suitable material, such as, for example, artificial cork, natural cork, or an EVA cork mixture.

Figure 11:
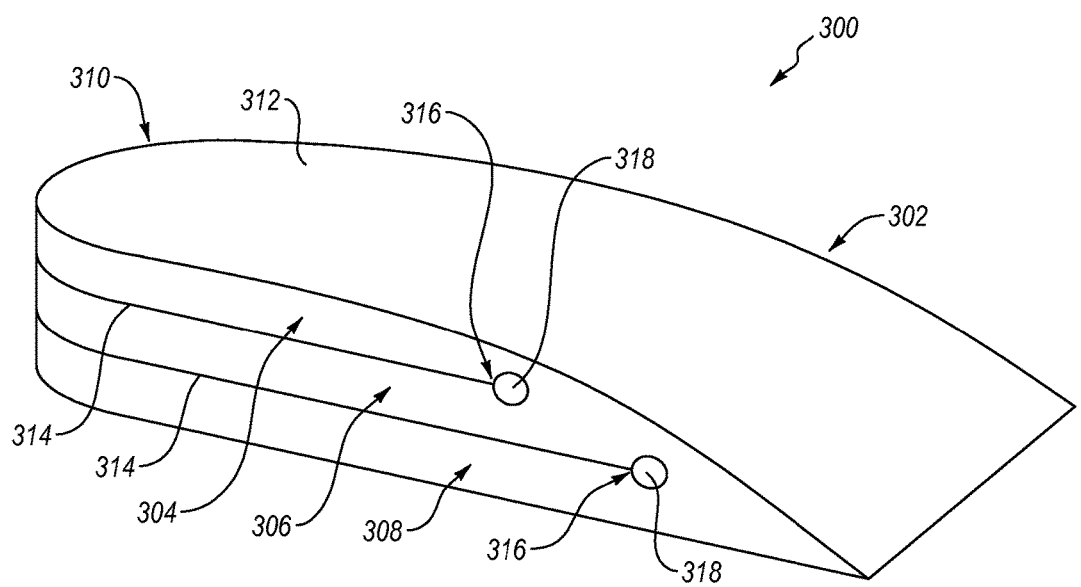
FIG. 11 represents a perspective view of another exemplary embodiment of an Achilles tendon stretching device in the form of an Achilles heel wedge having layers which can be removed to adjust the height of the heel wedge.
Figure 12:
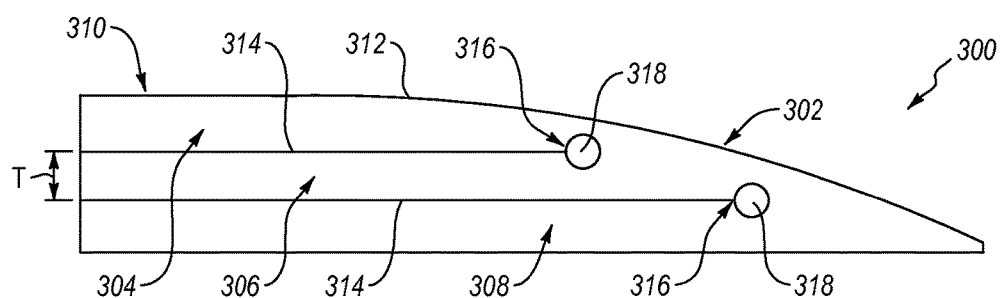
FIG. 12 is a side view of the Achilles heel wedge shown in FIG. 11.

Referring to FIGS. 11 and 12, the heel wedge 300 has a number of layers, all of which are integrally formed and connected together at an anterior portion 302 of the heel wedge 300. The layers are integrally connected rather being temporarily attached to another as in the prior art. This has effect of keeping the layers together when the heel wedge 300 is not being used so as to not be so easily misplaced. This also can help keep the layers in alignment during use.

As shown, the heel wedge 300 includes first layer 304, second layer 306, and third layer 308. However, the number of layers shown is merely exemplary, and any suitable greater or lesser number of layers, for example, two to fifteen layers, may be used in order to achieve the desired amount and increments of height adjustment.

In use, the heel wedge 300 can be positioned within the foot bed or heel portion of an orthopedic device with all of the layers thereof retained. Thus, the Achilles tendon of the user of the heel wedge 300 will he shortened to a first length. In order to incrementally stretch or the lengthen the Achilles tendon of the user of the heel wedge 300, the layers 304, 306, 308 thereof can be incrementally removed (e.g., cut, ripped, or torn) from the heel wedge 300 in order to reduce the height of the heel wedge 300, thus stretching the Achilles tendon of the user to incrementally greater lengths.

The thickness or height of the layers 304, 306, 308 correspond to the desired incremental stretch length of the Achilles tendon, and may be any desired thickness or height.

The heel wedge 300 can include the anterior portion 302, a posterior portion 310, and a foot support surface portion 312 extending between the anterior portion 302 and the posterior portion 310. Generally, the overall shape of the heel wedge 300 and/or the foot support surface portion 312 is configured to naturally and/or comfortably support the user's foot by better fitting the natural curve of the foot and/or controlling the foot angle. For instance, the layer 310 can include an upper surface configured to substantially fit the nature curve of the foot. In order to provide additional stability to the foot, a separate arch support can be attachable to the heel wedge 300. Other exemplary configurations of the overall shape of the heel wedge and arch support are described in U.S. provisional patent application 62/026,884, filed on Jul. 21, 2014, and herein incorporated in the entirety by reference.

Referring still to FIGS. 11 and 12, the heel wedge 300 can comprise a single or continuous member with partial cuts or slits 314 to differentiate each layer. The slits 314 can extend completely or at least in part between the lateral and medial sides of the heel wedge 300 and a distance along the longitudinal axis of the heel wedge 300. In an embodiment, the length of the slit 314 between the layers 306 and 308 can be longer than the slit 314 between the layers 306 and 304. The slits 314 also define a width or gap between the opposing sides of the slit. The layers can define at least in part the slits 314. For instance, as seen in FIG. 12, the layer 308 can include an upper surface portion and the layer 306 can include a lower surface portion defining at least in part the slit 314 between the layers 306 and 308. The layer 308 can include a lower surface portion substantially parallel the upper surface portion of the layer 308 and the layer 306 can include an upper surface portion substantially parallel to the lower surface portion of the layer 306. In other embodiments, at least one of the layers can include upper and lower surface portions that are not parallel.

At least one perforation 318 is situated at a terminal end 316 of each of the slits 314. The perforation 318 can have a dimension (e.g., a diameter, a length, a width) greater than the width of the slit 314. As discussed in more detail below, the perforations 318 are configured to relieve stress and/or aid in the removal of layers from the wedge 300.

The perforations can take numerous forms, such as a vertical cut to form a T-shape perforation. In the illustrated embodiment, the perforations comprise generally cylindrical holes 318, each having a diameter greater than the width of the slit 314. The holes 318 can extend completely between the lateral and medial side of the heel wedge 300. The holes 318 can extend in part between the lateral and medial side of the heel wedge 300. The holes 318 can be formed in any suitable manner. For instance, the holes 318 can be formed during the molding of the heel wedge 300 using one or more pins. Alternatively, the holes 318 can be formed subsequent to a molding process using secondary boring, drilling, and/or cutting operations.

At least one of the holes 318 can have a diameter that is greater than about 9 times the width of the slit 314. In other embodiments, at least one of the holes 318 can have a diameter that is greater than about 10 times, about 8 times, about 6 times, about 4 times, about 2 times, about 1.5 times, about 1.2 times, or about 1.1 times the width of the slit 314. It will be appreciated that the dimensions expressed herein are only exemplary and will vary depending on particular use. Further, the diameter of the hole 318 may be constant or vary. For instance, the diameter of the hole 318 may be larger toward the lateral and/or medial sides of the heel wedge.

A stress concentration is a local increase of stress created by some discontinuity at the surface or with the body a component. The sharper or more abrupt the change the greater the stress concentration. In the illustrated embodiment, the maximum stress concentration near the slits 314 theoretically would occur in the area of lowest radius of curvature or at sharp terminal ends of the slits 314. The hole 318, with its relatively larger diameter and greater radius of curvature, distributes stress over a larger area than a sharp terminal end, which, in turn, causes a smaller stress concentration. This has the effect of reducing unwanted ripping or tearing at the terminal ends 316 when the heel wedge 300 is under stress during use, substantially increasing the durability and/or usability of the heel wedge 300.

The shape of the holes 318 can also be configured to help decrease stress concentrations along the slits 314. For instance, the rounded shape of the hole 318 can create a smoother change or transition at the terminal end 316 where stress flow lines are less crowded (i.e., less concentrated) as compared to a sharper terminal end where stress flow lines more abruptly change and are more crowded (i.e., more concentrated). It should be appreciated that other factors such as, but not limited to, the material of the heel wedge 300, location of the holes 318, and/or the amount of material surrounding the holes 318 can also influence stress concentrations along the slit 314.

Figure 13:
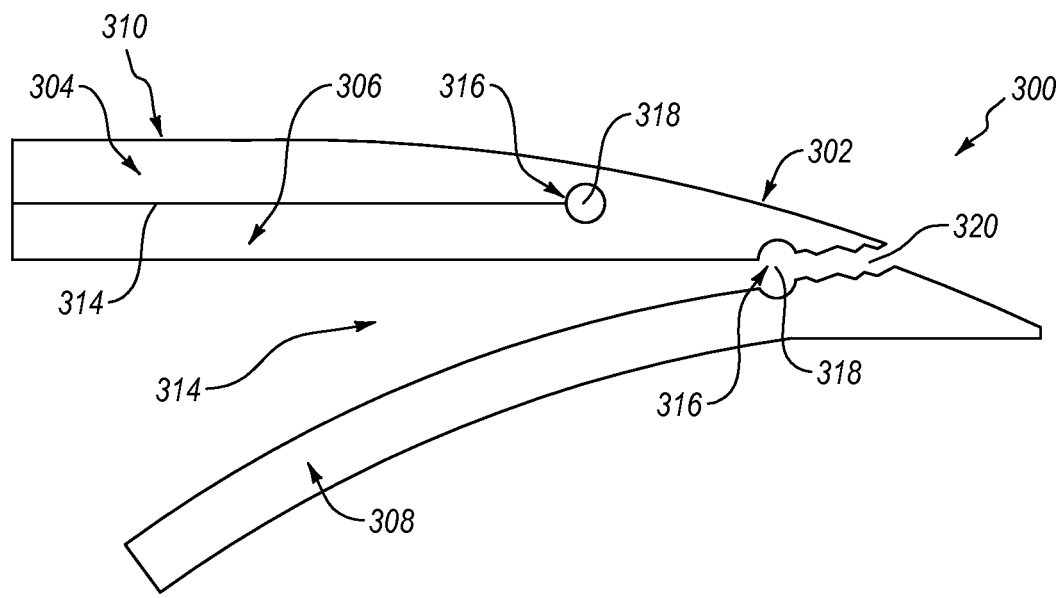
FIG. 13 is a side view of the Achilles heel wedge shown in FIG. 11 showing the bottom later being removed.
Figure 14:
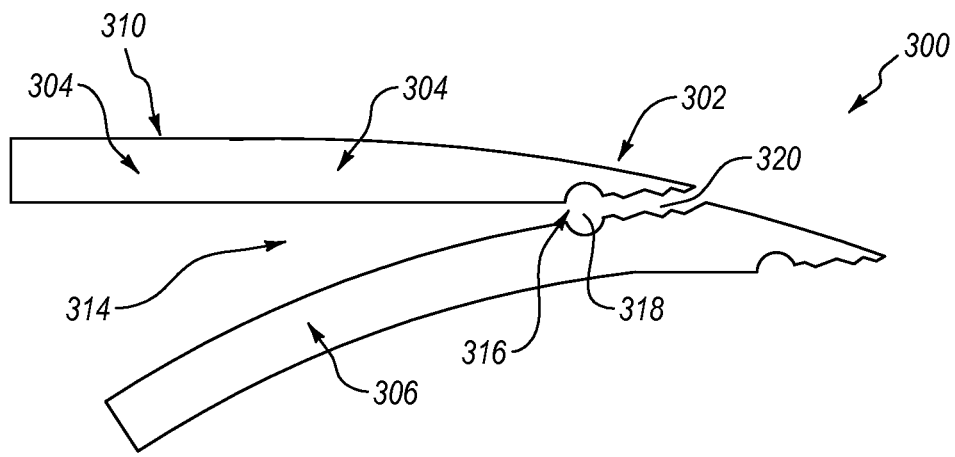
FIG. 14 is a side view of the Achilles heel wedge shown in FIG. 11 showing another layer being removed.

Referring now to FIGS. 13 and 14, the holes 318 can also aid in removal of the layers from the heel wedge 300. Similar to the layers 202, 204, 206, 208, the layers 30.4, 306, 308 can be incrementally removed from the heel wedge 300 in order to reduce the height of the heel wedge 300, thus stretching the Achilles tendon of the user to incrementally greater lengths. The layers 304, 306, 308 of the heel wedge 300 can be separated or torn apart along the holes 318, which, in turn, can guide the resulting separation or tear 320 transversely across the heel wedge 300. This has the effect of reducing the likelihood of layers 304, 306, 308 tearing or physically separating in undesirable locations and/or directions when being removed by a user, which, in turn, makes the heel wedge 300 easier to use. In an embodiment, the heel wedge 300 may have an average tear resistance along at least one of the holes 318 greater than about 1 kgf/cm, about 3 kgf/cm, about 10 kgf/cm, about 15 kgf/cm, about 20 kgf/cm, about 25 kgf/cm, about 40 kgf/cm, or 50 kgf/cm, or about 75 kgf/cm. In other embodiments, the tear resistance may be higher or lower.

It will be appreciated that the tear resistance can be defined at least in part by the material of the heel wedge 300 and/or the amount of material surrounding the holes 318. It will be further appreciated that removing the layers can include tearing the layers apart, cutting the layers apart, ripping the layers apart, combinations thereof, or separating the layers from the heel wedge 300 in any other suitable manner. Further, the tear 320 can comprise a tear, a rip, a cut, combinations thereof, or any other physical separation.

To adjust the stretch length of the Achilles tendon at a first time, the heel wedge 300 can be removed from the heel portion or foot bed of the orthopedic device as seen in FIG. 14. The layer 308 can be removed from the heel wedge 300 by cutting, ripping, and/or tearing the layer 308 away at the hole 318. As shown, the resulting separation or tear 320 can extend generally parallel to a bottom surface of the layer 306. It will be appreciated however that the tear 320 can extend in any suitable direction from the hole 318. For example, the tear 320 can extend radially upward, radially downward, radially outward, or in any other suitable direction from the hole 318.

The heel wedge 300 can then be replaced in the orthopedic device and treatment can occur for the desired length of time to stretch the Achilles tendon at the length that provided by removing the layer 302.

As shown in FIG. 14, this process can be repeated as necessary by removing layer 306 to treat Achilles tendon injuries and/or assist in surgical recovery with incremental stretching of the Achilles tendon, leaving the layer 304. The heel wedge 300 now comprising the layer 304 can be replaced in the orthopedic device for treatment. Alternatively, the heel wedge 300 comprising the layer 304 may be used after the orthopedic device is no longer needed. For instance, the heel wedge 300 comprising the layer 304 can be inserted into typical footwear (e.g., shoes or boots) without stressing a recently healed Achilles tendon, helping the user transition back into the typical footwear.

As discussed above, it should be noted that if greater height adjustment is needed during a specified treatment period, more than one of the layers 304, 306, 308 can be removed simultaneously. The thickness T (shown in FIG. 12) of the individual layers can be configured to fulfill requirements of specific therapeutic protocols where the foot must be placed in varying angles to achieve healing. For (example, each layer can have a thickness between about 7 mm and about 12 mm (e.g., about 10 mm). The thickness T of the individual layers can be thinner (e.g., between about 2 mm and about 6 mm) to allow for the application of custom therapeutic protocols where the layers are removed in response to a patient's progress during the course of therapy. It will be appreciated that the thickness T of the individual layers can be more or less.

Referring still to FIGS. 13 and 14, the holes 318 can also facilitate removal of the layers 304, 306, 308 by increasing the ability of the individual layers 304, 306, 308 to bend or move away from one another along the slits 314. This can allow the user to open or widen the slits 314 when removing layers from the wedge 300, providing greater physical and/or visual access to the user, which, in turn, makes it easier for the user to tear or remove the layers from the heel wedge 300.

Figure 15:
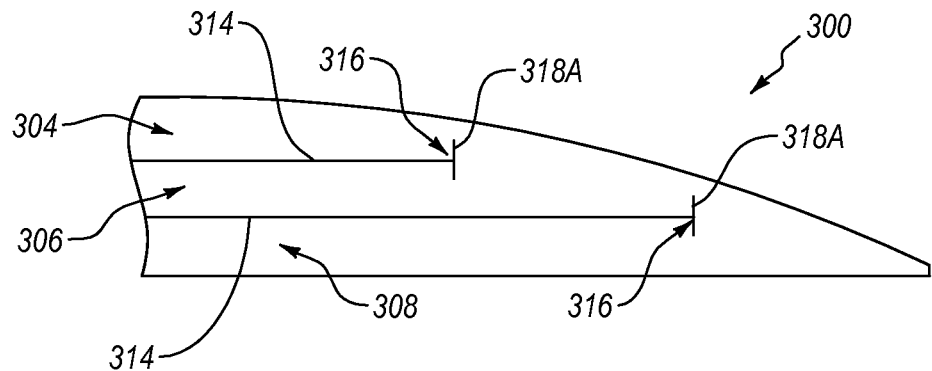
FIG. 15 is a partial side view of an Achilles heel wedge according to another embodiment.

It should be appreciated that many variations of the perforations 318 having different shapes and/or sizes can be used. Although such variations may differ in form, they perform substantially similar functions. The perforations 318 may be circular shaped as described, or may be rectangular, oblong, elliptical, diamond shaped, rounded rectangular shaped, or any other suitable shape. For instance, the perforation can comprise a T-shape perforation 318A as shown in FIG. 15. An advantage provided by a T-shape perforation 318A is that it reduces creation of waste cutout material during manufacturing of the heel wedge 300.

Figure 16:
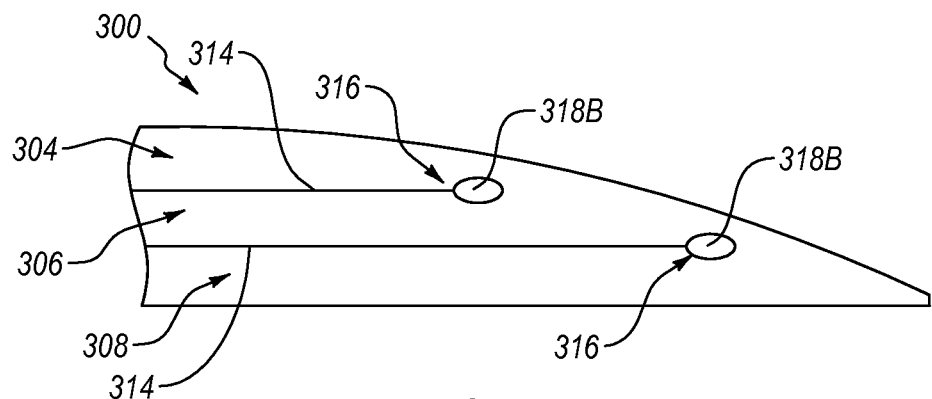
FIG. 16 is a partial side view of an Achilles heel wedge according to another embodiment.
Figure 17:
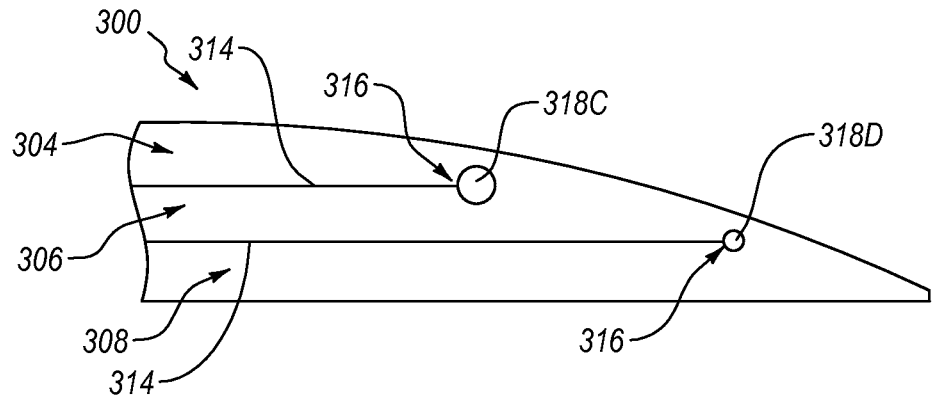
FIG. 17 is a partial side view of an Achilles heel wedge according to another embodiment.

In other embodiments, the perforation 318 can comprise a generally oval or oblong hole 318B with the longer axis oriented generally parallel to the slit 314 as shown in FIG. 16. The hole 318B advantageously can facilitate tearing generally parallel to the slit 314 or the upper surface of the layer as the heel wedge would be more likely to tear along the longer axis of the hole 318B due to the tighter radius of curvature.

In other embodiments, the size and/or shape of the perforations can vary between different layers. This has the effect of allowing the level of stress relief between different layers to vary. For instance, the perforation between the layers 304 and 306 can comprise a first generally cylindrical hole 318C having a first diameter and the perforation between the layers 306 and 308 can comprise second generally cylindrical hole 318D having a second diameter that is less than the first diameter. Because the first diameter is larger than the second diameter, the first hole 318C can distribute stress over a larger area to provide greater stress relief toward the foot support surface portion 312. This can be advantageous where eversion and/or inversion of the user's foot can create greater torsion between layers 304 and 306 than between layers 306 and 308.

G. Conclusion

It will be recognized that the exemplary embodiments of an Achilles tendon stretching device and components thereof can be made from any suitable materials.

While one week has been described above as a suitable time period for measuring when adjustment to the Achilles tendon stretching device should be made, it will be recognized that any suitable or desired time period may be utilized.

It will also be recognized that the various locations of each of the adjustment mechanisms of the exemplary Achilles tendon stretching devices described herein can be variously located in any convenient location, for example, at the posterior of the walker or in the plantar sole region of the walker.

While specific mechanical mechanisms (for example, a scissor jack or a socket head cap screw and universal joint) are described herein for adjusting the height of an insole with respect to the planter sole of a walker, any suitable mechanical, pneumatic, and/or hydraulic mechanism can be used to adjust the height of the insole. For example, pneumatic or hydraulic cylinders and pistons may be positioned between the insoles and plantar soles and used to raise and lower the adjustable height insoles. For example, a pneumatic or hydraulic cylinder and piston can be oriented to provide vertical translation to raise or lower the insole with respect to the plantar sole. Such pneumatic or hydraulic cylinders and pistons can be configured to automatically adjust height, either incrementally or continuously, as discussed in detail above with respect to alternatively recited configurations. The specific design and implementation of such pneumatic or hydraulic cylinders and pistons will be recognized by a person having skill in the art.

While the perforations of the heel wedge are described herein at the terminal ends of the slits, the perforations can be situated in any suitable location along or near the slits. For example, the perforations can be located along the slits proximal to the terminal ends. In other embodiments, the perforations can be located distal to the terminal ends and between the terminal ends and the foot support surface portion. In other embodiments, at least one of the perforations can comprise a plurality of perforations extending at least in part between the lateral and medial sides of the heel wedge and separated from one another by portions of the heel wedge. In other embodiments, one or more of the slits may not include a perforation. In yet other embodiments, one or more of the slits may include more than one perforation. For example, at least one of the slits may include two, three, four, or any of perforations distributed along the longitudinal axis of the heel wedge.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features from the disclosed embodiments and variations. In addition to variations described herein, other known equivalents for each feature can be mixed and matched by one of ordinary skill in this art to construct an Achilles tendon stretching device in accordance with principles of the present invention.

Although this invention has been disclosed in the context of exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. An Achilles heel wedge comprising:
a single member formed from a material and including:
an anterior portion;
a plurality of layers integrally connected at the anterior portion;
a plurality of slits differentiating the layers, each slit extending in a longitudinal direction to a closed end in the anterior portion; and
a plurality of perforations defining the closed ends of the slits in the anterior portion, each perforation having a length extending in a transverse direction between lateral and medial outer sides of the single member and having a dimension greater than a width of the slit, the perforations arranged to direct selective tearing of one or more of the layers from the single member at the anterior portion, wherein at least one of the perforations comprises an elongated hole having a diameter that varies between the lateral and medial sides of the single member.

2. The wedge of claim 1, wherein the layers of the heel wedge are configured to be selectively torn from the anterior portion of the single member to achieve incremental height adjustment of the heel wedge and stretching of the Achilles tendon.

3. The wedge of claim 1, wherein at least one of the perforations is configured to guide a tear or a rip transversely across the single member.

4. The wedge of claim 1, wherein at least one of the perforations is configured to guide a tear or a rip substantially parallel to at least one of the slits.

5. The wedge of claim 1, wherein an average tear resistance along the at least one of the perforations is greater than about 3 kgf/cm.

6. The wedge of claim 1, wherein the elongated hole is substantially cylindrical.

7. The wedge of claim 1, wherein two or more of the perforations have different shapes or sizes.

8. The wedge of claim 1, wherein at least one of the perforations comprises a vertical slit.

9. The wedge of claim 1, wherein at least one of the perforations has a substantially oblong cross-sectional shape.

10. The wedge of claim 1, wherein the heel wedge is sized and configured to be removably positioned in a foot bed of an orthopedic device.

11. The wedge of claim 10, wherein the orthopedic device comprises a walker boot.

12. The wedge of claim 1, wherein the layers comprise a top layer and bottom layers, and wherein the bottom layers are selectively removable from the top layer and the top layer is positionable in a shoe or boot.

13. An Achilles tendon treatment system comprising:
an orthopedic device including a foot bed;
an Achilles heel wedge removably positionable in the foot bed, wherein the heel wedge comprises:
a single member formed from a material and including
an anterior portion,
a plurality of layers integrally connected at the anterior portion, the plurality of layers including a top layer having a foot support surface portion configured to substantially fit a natural curve of a foot of a user;
a plurality of slits differentiating the layers, each slit extending in a longitudinal direction to a closed end in the anterior portion; and,
a plurality of perforations defining the closed ends of the slits in the anterior portion, each perforation having a length extending in a transverse direction between lateral and medial outer sides of the single member and having a dimension greater than a width of the slit, the perforations arranged to direct selective tearing of one or more of the layers, wherein at least one of the perforations comprises an elongated hole having a diameter that varies between the lateral and medial sides of the single member
wherein the layers of the heel wedge are configured to be selectively removed from the single member along the perforations to achieve incremental height adjustment of the heel wedge and stretching of the Achilles tendon.

14. The system of claim 13, wherein the plurality of layers includes a bottom layer having an upper surface portion defining in part at least one of the slits and a bottom surface portion substantially parallel to the upper surface portion.

* * * * *